United States Patent
Nauerth

(10) Patent No.: US 8,638,097 B2
(45) Date of Patent: Jan. 28, 2014

(54) INTERFERENCE COMPENSATION IN MR MEASUREMENTS ON MOVING OBJECTS THROUGH ADJUSTMENT OF THE MEASUREMENT CONDITIONS

(76) Inventor: Arno Nauerth, Erlenbach (DE)

( * ) Notice: Subject to any disclaimer, the term of this patent is extended or adjusted under 35 U.S.C. 154(b) by 372 days.

(21) Appl. No.: 12/929,596

(22) Filed: Feb. 3, 2011

(65) Prior Publication Data

US 2011/0199083 A1  Aug. 18, 2011

(30) Foreign Application Priority Data

Feb. 9, 2010  (DE) .......................... 10 2010 001 703

(51) Int. Cl.
*G01V 3/00* (2006.01)
(52) U.S. Cl.
USPC .......................................... 324/309; 324/312
(58) Field of Classification Search
USPC .................. 324/309, 312, 313, 314, 318, 322
See application file for complete search history.

(56) References Cited

U.S. PATENT DOCUMENTS

| | | | |
|---|---|---|---|
| 6,118,273 A * | 9/2000 | Takizawa et al. ............. | 324/309 |
| 6,894,494 B2 * | 5/2005 | Stergiopoulos et al. ...... | 324/309 |
| 8,138,759 B2 * | 3/2012 | Greiser et al. ................ | 324/309 |
| 2002/0156366 A1 | 10/2002 | Stainsby | |
| 2006/0224062 A1 | 10/2006 | Aggarwal | |
| 2007/0090837 A1 | 4/2007 | Van Der Kouwe | |
| 2007/0238972 A1 | 10/2007 | Nauerth | |

FOREIGN PATENT DOCUMENTS

| | | |
|---|---|---|
| EP | 1 488 248 | 12/2004 |
| WO | WO 01/84172 | 11/2001 |
| WO | 2007/106360 | 9/2007 |
| WO | 2007/124243 | 11/2007 |
| WO | 2009/074917 | 6/2009 |
| WO | 2009/129457 | 10/2009 |

OTHER PUBLICATIONS

Van Gelderen et al., "Real-time shimming to compensate for respiration-induced B0 fluctuations", pp. 362-368, INSPEC abstract 9373137, Magnetic Resonance in Medicine (2007), vol. 57.

* cited by examiner

*Primary Examiner* — Louis Arana
(74) *Attorney, Agent, or Firm* — Paul Vincent

(57) ABSTRACT

A method for generating magnetic resonance (MR) images or MR spectra of at least one partial area of a moving object with at least one motion sequence that is repeated during consecutive motion states is proposed. In a learning measurement, a monitor signal of the repeating motion sequence is recorded, and MR test data of the partial area of the object are recorded under known measurement conditions, wherein the MR test data is associated with the motion states of the motion sequence. In an evaluation step, the MR test data of the motion states of the motion sequence are compared to each other with respect to at least one parameter, and the variation of the at least one parameter over the motion sequence is determined. The instantaneous motion state of the object in the motion sequence is constantly determined in a target measurement during recording of the MR images or MR spectra of the partial area via a monitor signal, and the associated variation of the at least one parameter is constantly compensated for by corresponding variation of the measurement conditions. The quality of MR measurements for recording moving objects is thereby improved, in particular, when retroactive calculation of disturbances in the measured MR data is not possible.

19 Claims, 6 Drawing Sheets

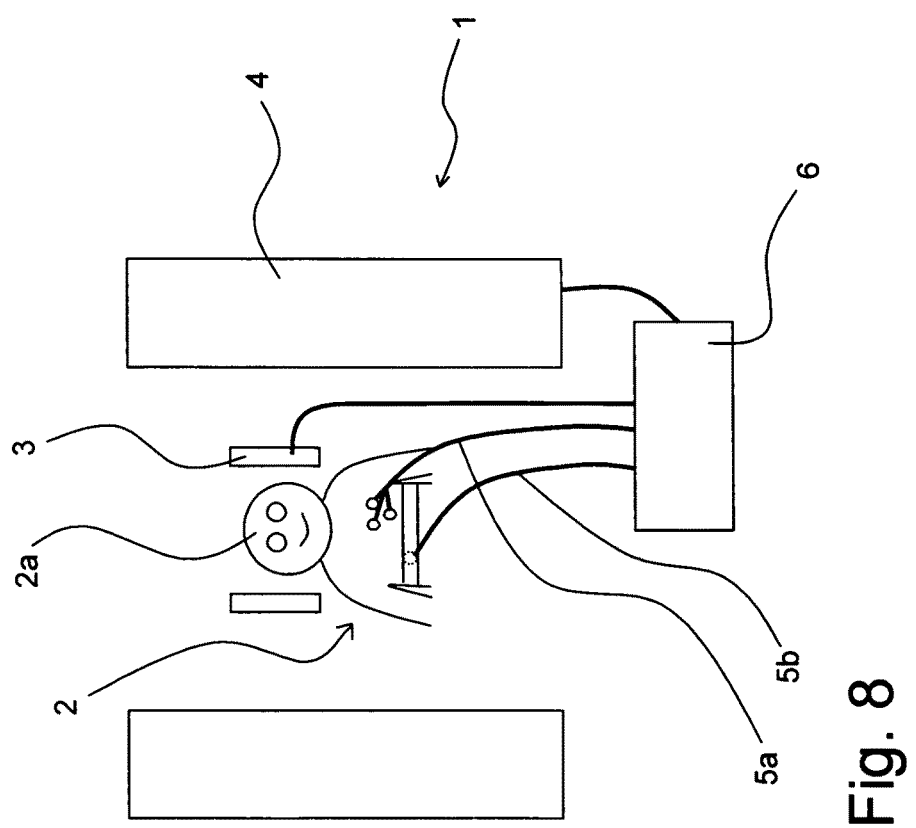

INTERFERENCE COMPENSATION IN MR MEASUREMENTS ON MOVING OBJECTS THROUGH ADJUSTMENT OF THE MEASUREMENT CONDITIONS

This application claims Paris Convention priority of DE 10 2010 001 703.5 filed Feb. 9, 2010 the complete disclosure of which is hereby incorporated by reference.

BACKGROUND OF THE INVENTION

The invention concerns a method for generating magnetic resonance (MR) images or MR spectra of at least one partial area of a moving object with at least one motion sequence that is repeated during consecutive motion states.

A method of this type has been disclosed in DE 10 2006 002 982 B4 (US patent application 2007/0238972 A1).

Magnetic resonance (MR) methods, in particular nuclear magnetic resonance (NMR) methods, are used for a wide variety of purposes for obtaining image information or also chemical information about objects. In clinical applications, living objects, e.g. human beings or animals or individual body parts of human beings and animals are thereby regularly examined.

When an object moves during the MR measurement, the quality of the measurement may be impaired. With respect to image recordings, the image may e.g. be blurred. In general, one tries to keep the object stationary during the measurement. Human patients may e.g. be asked not to move and animals may be anaesthetized.

Some motion processes, usually repetitive motion processes, are part of the basic functions of life and cannot be avoided, such as e.g. the heart beat or respiration.

In order to reduce the influence of repetitive motions on an MR measurement, the motions of the object are normally monitored and the MR measurements are performed within a time slot, in which the motion is interrupted or is at a minimum, e.g. between two heart beats. The MR measurements are then triggered via a suitable monitor signal.

However, it is sometimes desired to precisely observe changes in an object during a repetitive motion sequence. The changes in the object during such a repetitive motion sequence are generally relatively small such that the deteriorated quality of the MR measurement caused by the motion renders observation of these changes impossible.

DE 10 2006 002 982 B4 (US patent application 2007/0238972 A1) discloses determination of one function f(t) of the time shift for each individual MR image and phase-correcting the measured data of the individual MR images in correspondence with their motion state. It is thereby possible to keep the position of a moving partial area in a spatially stationary state after data processing.

This procedure can improve the data quality only in a limited number of situations. When e.g. slice selection is used within the scope of the MR measurement, compensation can be effected through back calculation only in the plane. When the motion of the object disturbs measurement variables other than direct motion of the object per se, e.g. a time variation of the local strength of a gradient field, the disturbance in the individual MR images cannot be back calculated and the quality of the measured MR data cannot be improved.

It is therefore the underlying purpose of the present invention to provide a method for improving the quality of MR measurements of moving objects, in particular, when back calculation of disturbances in the measured MR measured data is not possible.

SUMMARY OF THE INVENTION

This object is achieved by a method for generating magnetic resonance (MR) images or MR spectra of at least one partial area of a moving object with at least one motion sequence that is repeated during consecutive motion states,
a) wherein in a learning measurement
  a monitor signal of the repeating motion sequence is recorded, and
  MR test data of the partial area of the object is recorded under known measurement conditions, wherein the MR test data is associated with the motion states of the motion sequence, in particular, wherein the MR test data is in the form of images or projections of the partial area,
b) wherein, in an evaluation step, the MR test data of the motion states of the motion sequence are compared to each other with respect to at least one parameter, the one parameter encompassing the static magnetic field $B_0$ and/or a magnetic field gradient of first and/or higher order, and the change of the at least one parameter during the motion sequence is determined,
c) and wherein, in a target measurement during recording of the MR images or MR spectra of the partial area, the instantaneous motion state of the object in the motion sequence is constantly determined via a monitor signal, and the associated variation, determined in step b), of the at least one parameter is constantly compensated for by a corresponding variation of the measurement conditions. The compensation of the parameter is effected continuously and asynchronously with respect to recording of the MR-images and is controlled by the monitor signal in combination with the change in the parameter(s) during the motion sequence (e.g. the magnet field $B_0$) as determined in step b).

Within the scope of the present invention, disturbances caused by motions of objects are compensated for in that the measurement conditions under which the MR data is recorded, are changed during the actual measurement (target measurement). This change of the measurement conditions is controlled by means of a monitor signal that is typically continuously detected during the target measurement. The monitor signal gives information about the instantaneous motion state, i.e. the degree of progression, in the repeating motion sequence.

Within the scope of the learning measurement and the evaluation step, associated parameter values (disturbance parameters) are determined for the various motion states of the object via MR test data. The MR test data (sets) is (are) typically MR test images or also projections (in particular, one-dimensional projections) of the partial area. In order to compensate for the variation of these values (e.g. compared to the start of the repeating motion sequence), adjusted measurement conditions are further determined for the various motion states. Each adjusted measurement condition minimizes or completely eliminates the effects of the changed values of the parameters on the target measurement.

The inventive method at least largely renders the measured MR data of the target measurement independent of the disturbances caused by the motion of the object. Since the measurement conditions are adjusted to the instantaneous motion state, disturbances of any type can be compensated for. Since the compensation is already effected during the target measurement, information loss caused by recording of non-compensated MR data cannot happen. Retrospective correction of MR data from a target measurement is not necessary.

When there are several independent motion sequences to be compensated for, the inventive method is applied with respect to each such motion sequence. i.e. in a) and b) the effect on at least one (disturbing) parameter is determined with respect to all respective motion sequences, and the instantaneous motion state with respect to all motion sequences is determined in the target measurement by means of a corresponding number of monitor signals, and the measurement conditions are correspondingly changed simultaneously in the target measurement for compensation of the previously determined parameter changes.

In a preferred variant of the inventive method, the moving object is an animal or a human being. Suitable animals are, in particular, rodents such as mice and rats, but also primates. It should be noted that typically only individual body zones of the object move during the period of investigation and other body zones remain stationary. The partial area from which MR images or MR spectra are generated may be selected from a moving body zone or a body zone that is stationary. Motion outside of the partial area may thereby cause, however, a disturbance in the partial area, which must be compensated for.

In a preferred variant, the at least one repeating motion sequence is the heart beat, breathing, swallowing and/or blinking. These motion sequences can be well compensated for by the inventive method, since the sequences of the various repetitions thereof are very similar. Breathing, e.g. lifts and lowers the chest of animals and human beings, thereby changing the spatial susceptibility distribution. This, in turn, also causes, in particular, a change in the static magnetic field of locations remote from the chest. The repeating motion sequence can moreover also be based on other physiological processes.

In a particularly preferred method variant, the at least one parameter comprises
the static magnetic field $B_0$,
a magnetic field gradient of first and/or higher order.

These parameters determine the most important disturbances caused by moving objects during the detection of MR data from substantially stationary regions.

In another advantageous embodiment, the measurement conditions for compensating for the variation in the at least one parameter are changed by
shifting the main frequency,
shifting the static magnetic field $B_0$,
changing the magnetic field gradient,
changing the gradients with respect to object motion,
and/or shifting the transmitting or receiving frequency or phase.

These changes in the measurement conditions compensate for the most important disturbances in the detection of MR data of moving objects. The change in the measurement conditions can also be calculated with respect to the object coordinate system or the patient coordinate system.

In one particularly preferred variant, a control signal is recorded during target measurement, the control signal displaying non-compensated disturbances, and MR images or MR spectra of the partial area are completely or partially discarded, or the recordings thereof are repeated when the control signal is outside of a previously defined value range during the recording. This procedure prevents errors in the measured MR data e.g. caused by unpredictable motions like hiccups. A control signal may e.g. be the strength of the static magnetic field at a defined location within the partial area. The control signal should remain approximately constant during a target measurement by tracking the static magnetic field during the measurement in correspondence with the instantaneous motion state. When the control signal leaves the previously defined value range, this indicates that compensation is incomplete. In accordance with the invention, the compensation could e.g. be limited to the most frequent repeating motion sequences such as heart beat and breathing (in order to reduce the calculation effort of the method) and upon occurrence of a rare repeating motion sequence such as swallowing or hiccup, the target measurement in accordance with this variant is simply suspended.

One particularly preferred method variant is characterized in that the object is subjected to several independent repetitive motion sequences, and with allocation of MR test data to motion states in one of the motion sequences, only MR test data is evaluated that belongs to the same motion state with respect to all other motion sequences in accordance with their respective monitor signal. In this fashion, the changes in the at least one parameter with respect to one single repeating motion sequence can be easily and individually detected. A series of MR test images (in the form of MR test data sets) could e.g. be assembled during the course of one heart beat exclusively from MR test images, which were each recorded exactly at the start of different breaths. It should be noted that during the learning measurement, a much larger number of MR test data sets might be recorded than are used in the evaluation step.

In another preferred variant, the MR images or MR spectra are respectively NMR images or NMR spectra. As an alternative to nuclear magnetic resonance (NMR), the invention can also be used in connection with electron spin resonance (ESR).

The present invention also concerns an MR apparatus, in particular, an MRI apparatus or MR spectrometer, which is designed to perform an inventive method as presented above. This apparatus produces MR data of improved quality from moving objects in a simple fashion.

Further advantages of the invention can be extracted from the description and the drawings. The features mentioned above and below may be used in accordance with the invention either individually or collectively in arbitrary combination. The embodiments illustrated and described are not to be taken as an exhaustive enumeration but have exemplary character for describing the invention.

The invention is illustrated in the drawing and explained in more detail with reference to embodiments.

BRIEF DESCRIPTION OF THE DRAWING

FIG. 8 shows a schematic view of an inventive MR apparatus for performing the inventive method.

DESCRIPTION OF THE PREFERRED EMBODIMENT

The inventive method is explained below with reference to an example. In the example, NMR images of the brain of a monkey shall be recorded while the monkey is breathing e.g. for examining metabolic processes during a breathing cycle. For this reason, the images cannot be recorded in breathing pauses. The motion of the monkey's chest, which is close to the brain of the monkey, also changes the magnetic fields (in particular, the $B_0$ field and the gradient fields of first order) in the area of the brain of the monkey (which itself is stationary since the monkey's head is fixed), such that the breathing motion of the monkey threatens to impair the quality of the images. However, the inventive method nevertheless generates good NMR images of the monkey's brain, since the inventive method compensates for or at least reduces the introduced disturbances.

Learning Measurement

Figure 1:
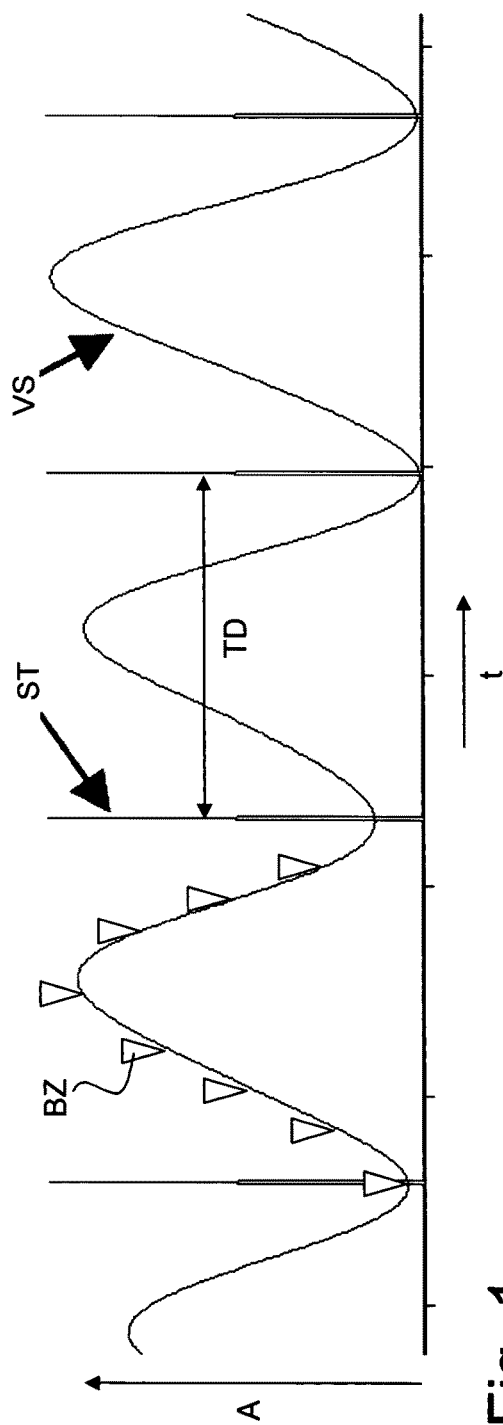
FIG. 1 shows a diagram of the time behavior of monitor signals (in the present case a breathing signal and a breathing signal trigger) over several cycles of a repeating motion sequence (in the present case breathing) in accordance with the inventive method.

For performing the inventive method, a so-called monitor signal of a repeating motion sequence (in the present case the breathing motion) of a moving object (in the present case the monkey) is initially recorded. FIG. 1 shows two monitor signals, which are suited for the invention, over three complete cycles of the motion sequence, in the present case, breathing of a monkey. The time t is shown towards the right-hand side in FIG. 1, and the amplitude A of the monitor signal is shown in the vertical direction.

When the motion sequence is very regular (with approximately constant duration TD of the cycles), the monitor signal can be limited to a signal trigger ST. Each signal trigger ST marks (in the present case) the start of a motion cycle for a period with a high amplitude ("peak"), which is short compared to the duration TD of the motion cycle. Otherwise, the amplitude is zero. The progression within a motion cycle, i.e. reaching the respectively consecutive motion states, is determined over the time that has lapsed since the last peak.

However, the progression within a motion cycle is preferably determined via reaching defined measured values of a constantly determined monitor signal, cf. the behavior signal VS with eight marked motion states BZ in FIG. 1. The behavior signal VS constantly detects the progression within one motion cycle via an associated change in signal amplitude. The behavior signal is generally based on the measurement of a physical value on the object, which varies and the variation of which can be well measured during the overall motion cycle with progression in the motion cycle. Fluctuations in the duration TD of the cycles can therefore also be well detected and compensated for. Calibration errors ("linear offset") can be reduced or avoided through evaluation of derivatives of the monitor signal.

When the monkey is breathing, a pressure sensor is e.g. used for generating a monitor signal. Breathing may also be optically monitored or in any other fashion. A recorded behavior signal is typically analogous and can, if desired, be converted into a signal trigger.

MR test data (sets), in the present case MR test images of the interesting partial area (in the present case the monkey's brain) of the object is (are) recorded at the same time (parallel) as the monitor signal is recorded. The MR test images are suitable for identifying disturbances of MR measurements that result from the repeating motion sequence of the object, e.g. field changes of zero and first order. Depending on the requirements for the target measurement, the data recording during the learning measurement generally consists of several 1D projections in different spatial directions or also of several 2D or 3D images.

Figure 2:
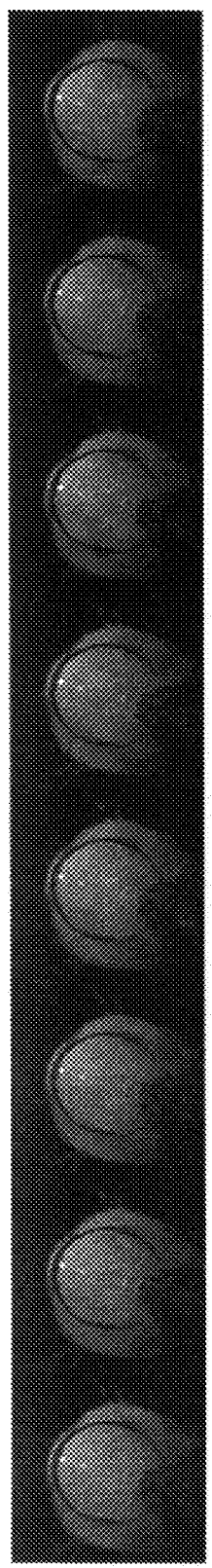
FIG. 2 shows eight magnitude images determined through NMR experiments (in the present case an axial oriented view through the brain of a monkey) for associated eight consecutive motion states within one breathing cycle ("breathing movie") in accordance with the inventive method.
Figure 3:
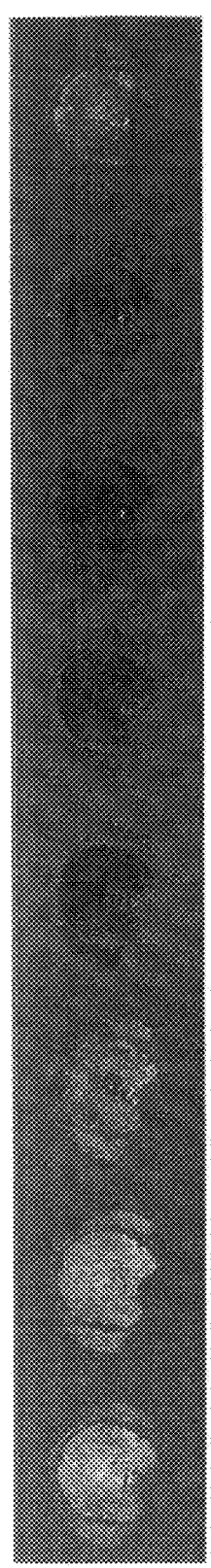
FIG. 3 shows eight phase images associated with the magnitude images of FIG. 2.

The MR test images are associated with the motion states of the motion cycle via the monitor signal. By way of example, FIGS. 2 and 3 show the MR test images of eight motion states over time during a breathing cycle of a monkey, wherein the images are sorted by time from the left-hand side to the right-hand side, with the start being on the left-hand side and the end of the cycle on the right-hand side.

It should be noted that each image can also be obtained by acquiring several images at the same motion state. Each image shows a slice of the brain of the monkey, wherein FIG. 2 shows the magnitude images and FIG. 3 shows the phase images. While the magnitude images of FIG. 2 seem to be approximately identical, the phase images of FIG. 3 show a clear influence of breathing on the measured data.

Evaluation Step

Figure 4A:
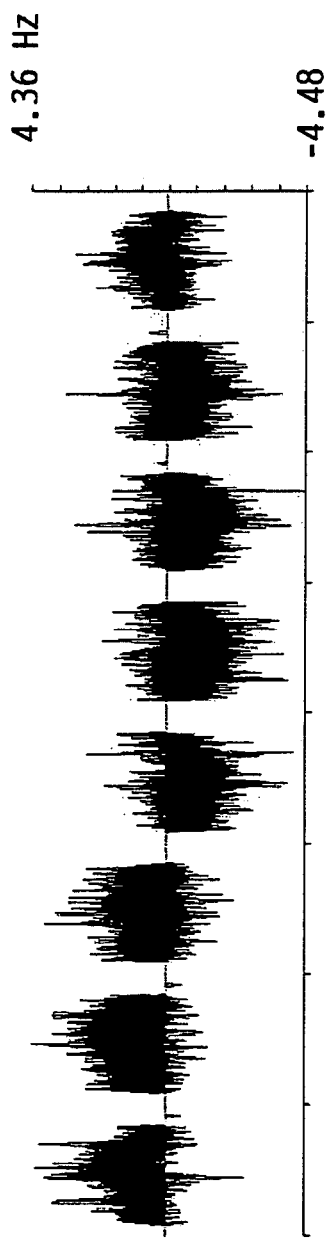
FIG. 4a shows a diagram of eight plots, which illustrates the weighted average value of all horizontal line points of the images of FIG. 3.
Figure 4B:
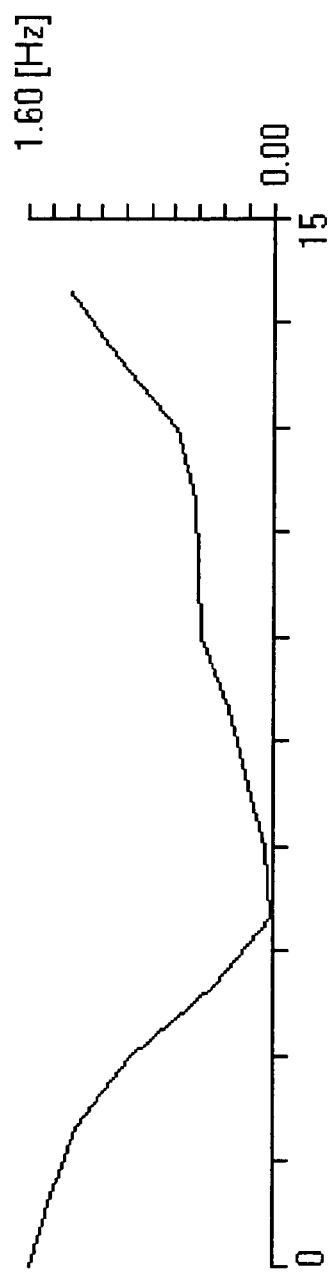
FIG. 4b shows a diagram of the local field change of 0 order ($B_0$ field) in the unit Hz as a function of the motion state or the time within one breathing cycle.

For preparing the target measurement, the MR test images are evaluated. The plots illustrated in FIG. 4*a* (sorted as in FIG. 3) show the weighted average value of all horizontal line points of the images of FIG. 3. A shim error of zero order can be determined therefrom after formation of an average value in the line direction. FIG. 4*b* correspondingly shows the influence of breathing (shown in the present case in sixteen motion states in temporal succession over one breathing cycle, plotted towards the right) on the so-called $B_0$ field, which is illustrated by a deviation of the resonance frequency (plotted towards the top). Linear interpolation was thereby performed for each motion state between the points of interpolation. The change in the $B_0$ field is a parameter that varies over the motion states (or the motion sequence), and can disturb the recording of MR images ("disturbance parameter").

Figure 5:
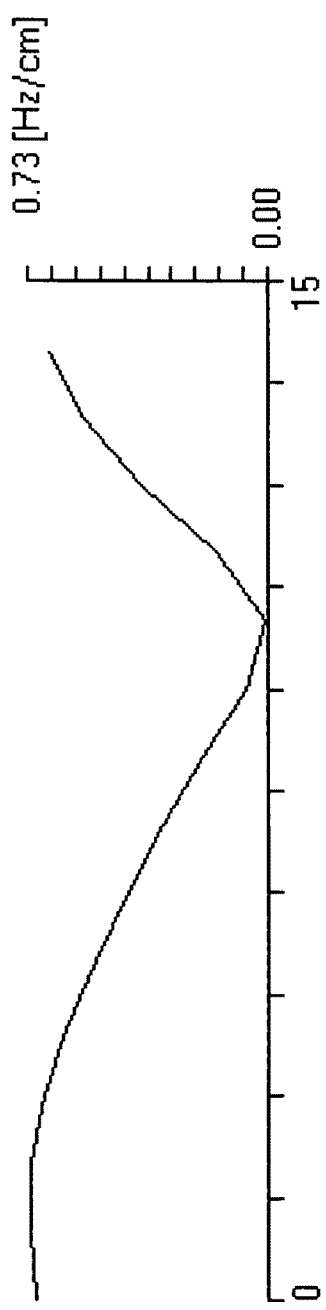
FIG. 5 shows a diagram of the local field change of first order in X direction (from the left to the right hand side in FIG. 3), in the present case given in units of the associated NMR frequency per length (Hz/cm) as a function of the motion state or the time within one breathing cycle.
Figure 6:
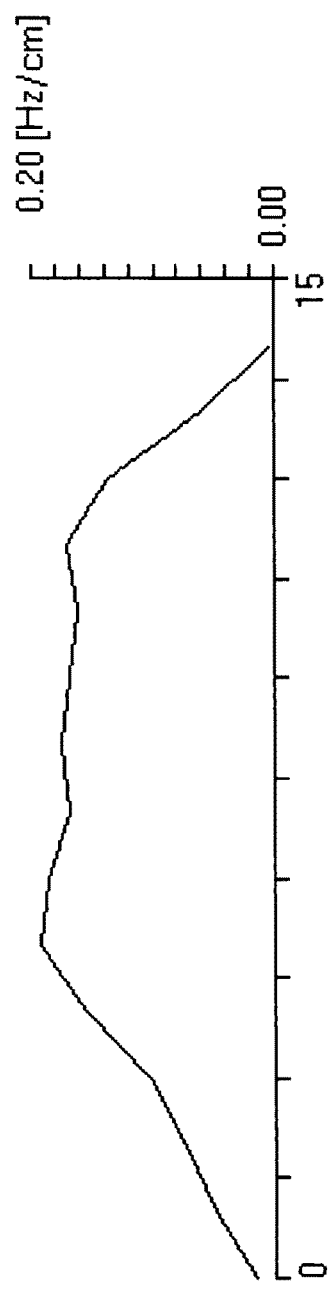
FIG. 6 shows a diagram of the local field change of first order in the Y direction (from the top to the bottom in FIG. 3) in the present case given in the unit Hz/cm, as a function of the motion state or the time within one breathing cycle.
Figure 7:
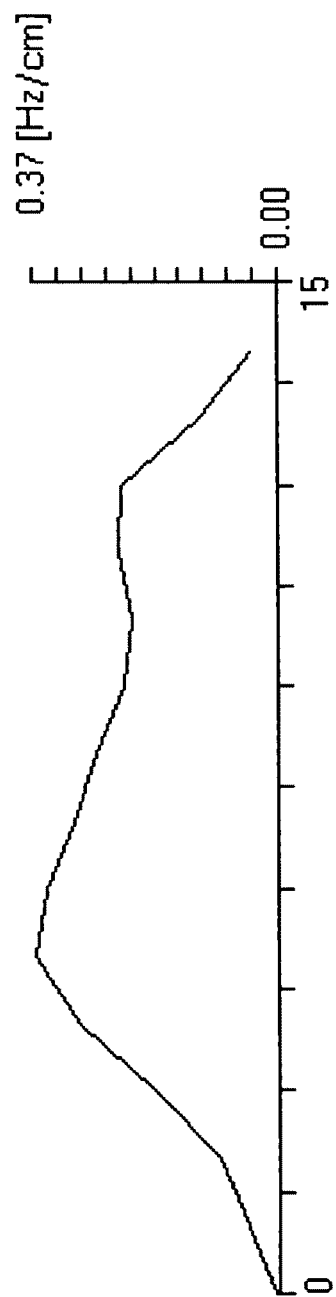
FIG. 7 shows a diagram of the local field change of first order in the Z direction, in the present case given in the unit Hz/cm as a function of the motion state or the time within one breathing cycle, which was determined from a further measurement, which is not shown in the drawing.

In a similar fashion it is possible to determine changes in the field gradients of first order in the X direction (FIG. 5), furthermore changes in the field gradients of first order in the Y direction (FIG. 6), and changes in the field gradients of first order in the Z direction (FIG. 7, the latter with a further learning measurement) over the motion sequence (in the present case divided into sixteen motion states). It is also possible to determine higher orders of field variations, thereby preparing compensation thereof. The field variations can be determined by a polynomial fit up to the corresponding order. It is clear that the number of motion states per cycle can be adjusted to the accuracy requirements for the disturbance compensation.

Target Measurement

The measurement conditions can be constantly adjusted (asynchronously) by means of the determined frequency errors of zero order of FIG. 4*b* during the actual measurement (target measurement) of the MR image or MR spectrum. In the simplest case, the external system frequency (in the present case the one predetermined by the MRI system) is varied during the motion sequence such that, in combination with the frequency error that is present in each respective current motion state, an effective system frequency is always obtained, which is constant to good approximation.

In an alternative fashion, the main field coil can be driven in such a fashion that the field strength of the $B_0$ field generated by it varies with time in such a fashion that, in combination with the instantaneous error of zero order of the $B_0$ field, an effective $B_0$ field, which is constant to good approximation, is obtained in the examined partial area of the moving object.

In a similar fashion, the gradient coils of the NMR system can be driven during the target measurement in such a fashion that the field gradients of first order remain effectively constant during the target measurement. It should be noted that disturbances in the field gradients can only be effectively eliminated by a correction of the measurement conditions during the operating time (and not by post processing).

For correction, a monitor signal of the object is again recorded parallel to the target measurement, the monitor signal being used to determine the respective instantaneous motion state in the motion sequence of the object (which corresponds substantially to the motion sequence of the learning measurement due to its repetition). The monitor signal may again be present in the form of a signal trigger or preferably a behavior signal (see above). The instantaneously active disturbance, i.e. the disturbance parameter, may be continuously determined with the instantaneous motion state from the existing data (from the learning and evaluation phase). The disturbance parameter then produces suitable measurement conditions (operating conditions of the NMR system) which compensate for the disturbance. These suitable measurement conditions are used for the current target measurement. It should be noted that suitable measurement conditions for a defined disturbance can be previously determined in the evaluation step or (if required) not earlier than during the target measurement.

The target measurement yields measured data of high quality through constant compensation of the disturbances caused by the motion of the object already during generation of the measured data through adjustment of the external measurement conditions to the motions, in particular, asynchronous readjustment (based on the evaluation of a monitor signal) of the magnetic fields of zero and higher orders. The measurements need no longer be performed in motion pauses and measured data can, in particular, also be recorded as a function of motion.

It should be noted that within the scope of the invention, one or even more disturbance parameters can be detected and compensated for each repeating motion sequence. It is also possible to simultaneously monitor several repeating motion sequences and to compensate the associated disturbances independently of each other.

FIG. 8 shows a highly schematized view of a magnetic resonance apparatus 1 for performing the inventive method. A partial area 2a (in the present case the head) of an object 2 (in the present case a monkey) is examined using magnetic resonance (in the present case NMR=nuclear magnetic resonance). Towards this end, an RF coil system 3 and a main field coil 4 are used amongst other things. Sensors 5a, 5b are provided on the object, which observe the motions of the object 2, in the present case the heart beat and breathing. In the illustrated embodiment, a so-called ECG signal is determined by three electrodes, wherein one electrode is fastened to the left-hand side and one is fastened to the right-hand side of the heart and one electrode is fastened below the apex. In this embodiment, the breathing signal is moreover determined by a pressure sensor which is arranged below a strap which is tightened around the chest or the diaphragm. The associated monitor signals are transferred to a control unit 6. During MR target measurements, the control unit 6 can compensate for disturbances which are caused by motion and are associated with the motion states of the object 2 detected by the monitor signals using learning measurements, through adjustment of the measurement conditions, e.g. the system frequency on the RF coil system 3 or the field strength in the main field coil 4. The control unit 6 comprises e.g. a trigger server which provides trigger information asynchronously with respect to the NMR measuring sequence, and a trigger client which adjusts compensation values in dependence on the requested trigger information.

Within the scope of the present invention, MR images or MR spectra can be generated. The quality of these MR images or MR spectra would be decreased when repeating motion is present. The invention however compensates for or at least improves the quality during the entire time of generation.

I claim:

1. A method for generating magnetic resonance (MR) images or MR spectra of at least one partial area of a moving object having at least one repeating motion sequence that is repeated during consecutive motion states, the method comprising the steps of:
   a) recording a monitor signal of the repeating motion sequence;
   b) recording MR test data of the partial area of the object under known measurement conditions;
   c) associating the MR test data, recorded in step b), with the motion states of the repeating motion sequence;
   d) comparing the MR test data of the motion states to each other with respect to at least one parameter, the one parameter encompassing a static magnetic field $B_0$, a magnetic field gradient of first order and/or a magnetic field gradient of higher order;
   e) determining a variation of the at least one parameter over the motion sequence;
   f) recording MR images or MR spectra of the partial area;
   g) constantly determining, during step f), an instantaneous motion state of the object in the motion sequence via the monitor signal; and
   h) constantly compensating, during step f), for the variation, determined in step e), of the at least one parameter by corresponding variation of the measurement conditions, wherein, during step f), a control signal is recorded which shows non-compensated disturbances, and MR images or MR spectra of the partial area are entirely or partially discarded or the recordings thereof are repeated when the control signal is outside of a predefined value range during the recording.

2. The method of claim 1, wherein the MR test data is in the form of images or projections of the partial area.

3. The method of claim 1, wherein the partial area is substantially stationary during the motion sequence.

4. The method of claim 2, wherein the partial area is substantially stationary during the motion sequence.

5. The method of claim 1, wherein the moving object is an animal or a human being.

6. The method of claim 2, wherein the moving object is an animal or a human being.

7. The method of claim 3, wherein the moving object is an animal or a human being.

8. The method of claim 1, wherein the at least one repeating motion sequence is based on heart beat, breathing, swallowing and/or blinking.

9. The method of claim 2, wherein the at least one repeating motion sequence is based on heart beat, breathing, swallowing and/or blinking.

10. The method of claim 3, wherein the at least one repeating motion sequence is based on heart beat, breathing, swallowing and/or blinking.

11. The method of claim 5, wherein the at least one repeating motion sequence is based on heart beat, breathing, swallowing and/or blinking.

12. The method of claim 1, wherein the measurement conditions are changed for compensating for variation of the at least one parameter by shifting the main frequency, shifting the static magnetic field $B_0$, changing a magnetic field gradient of first order or changing a magnetic field gradient of higher order.

13. The method of claim 2, wherein the measurement conditions are changed for compensating for variation of the at least one parameter by shifting the main frequency, shifting the static magnetic field $B_0$, changing a magnetic field gradient of first order or changing a magnetic field gradient of higher order.

14. The method of claim 3, wherein the measurement conditions are changed for compensating for variation of the at least one parameter by shifting the main frequency, shifting the static magnetic field $B_0$, changing a magnetic field gradient of first order or changing a magnetic field gradient of higher order.

15. The method of claim 5, wherein the measurement conditions are changed for compensating for variation of the at least one parameter by shifting the main frequency, shifting the static magnetic field $B_0$, changing a magnetic field gradient of first order or changing a magnetic field gradient of higher order.

16. The method of claim 8, wherein the measurement conditions are changed for compensating for variation of the at least one parameter by shifting the main frequency, shifting the static magnetic field $B_0$, changing a magnetic field gradient of first order or changing a magnetic field gradient of higher order.

17. The method of claim 1, wherein the object is subjected to several independent repeating motion sequences, and upon allocation of MR test data to motion states in one of the motion sequences, only MR test data is evaluated which belongs to a respectively identical motion state with respect to all other motion sequences in accordance with their respective monitor signal.

18. The method of claim 1, wherein the MR images or MR spectra are NMR images or NMR spectra.

19. An MR apparatus, MRI apparatus or MR spectrometer for generating magnetic resonance (MR) images or MR spectra of at least one partial area of a moving object having at least one repeating motion sequence that is repeated during consecutive motion states, the apparatus or spectrometer comprising:
  means for recording a monitor signal of the repeating motion sequence;
  means for recording MR test data of the partial area of the object under known measurement conditions;
  means for associating the MR test data with the motion states of the repeating motion sequence;
  means for comparing the MR test data of the motion states to each other with respect to at least one parameter, the one parameter encompassing a static magnetic field $B_0$, a magnetic field gradient of first order and/or a magnetic field gradient of higher order;
  means for determining a variation of the at least one parameter over the motion sequence;
  means for recording MR images or MR spectra of the partial area;
  means for constantly determining an instantaneous motion state of the object in the motion sequence via the monitor signal; and
  means for constantly compensating for the variation of the at least one parameter by corresponding variation of the measurement conditions, wherein a control signal is recorded which shows non-compensated disturbances, and MR images or MR spectra of the partial area are entirely or partially discarded or the recordings thereof are repeated when the control signal is outside of a predefined value range during the recording.

* * * * *

UNITED STATES PATENT AND TRADEMARK OFFICE
CERTIFICATE OF CORRECTION

| | |
|---|---|
| PATENT NO. | : 8,638,097 B2 |
| APPLICATION NO. | : 12/929596 |
| DATED | : January 28, 2014 |
| INVENTOR(S) | : Arno Nauerth |

Page 1 of 1

It is certified that error appears in the above-identified patent and that said Letters Patent is hereby corrected as shown below:

Title page, item "(76)" should read item -- (75) --.

Please amend the Title Page of the patent to add the Assignee as follows --

(73) Assignee: Brucker BioSpin MRI GmbH, Ettlingen (DE)

Signed and Sealed this
Seventeenth Day of March, 2015

Michelle K. Lee
*Director of the United States Patent and Trademark Office*

UNITED STATES PATENT AND TRADEMARK OFFICE
CERTIFICATE OF CORRECTION

PATENT NO. : 8,638,097 B2  
APPLICATION NO. : 12/929596  
DATED : January 28, 2014  
INVENTOR(S) : Arno Nauerth Page 1 of 1

It is certified that error appears in the above-identified patent and that said Letters Patent is hereby corrected as shown below:

Title page, item "(76)" should read item -- (75) --.

Please amend the Title Page of the patent to add the Assignee as follows --

(73) Assignee: Bruker BioSpin MRI GmbH, Ettlingen (DE)

This certificate supersedes the Certificate of Correction issued March 27, 2015.

Signed and Sealed this  
Twenty-first Day of April, 2015

Michelle K. Lee  
*Director of the United States Patent and Trademark Office*